(12) United States Patent
Kato et al.

(10) Patent No.: US 10,234,370 B2
(45) Date of Patent: Mar. 19, 2019

(54) PARTICLE SIZE MEASURING METHOD AND DEVICE

(71) Applicant: National Institute of Advanced Industrial Science and Technology, Tokyo (JP)

(72) Inventors: Haruhisa Kato, Tsukuba (JP); Naoko Oouchi, Tsukuba (JP); Ayako Nakamura, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 15/561,269

(22) PCT Filed: Mar. 30, 2016

(86) PCT No.: PCT/JP2016/060479
§ 371 (c)(1),
(2) Date: Sep. 25, 2017

(87) PCT Pub. No.: WO2016/159131
PCT Pub. Date: Oct. 6, 2016

(65) Prior Publication Data
US 2018/0120214 A1 May 3, 2018

(30) Foreign Application Priority Data
Mar. 30, 2015 (JP) .................................. 2015-069016

(51) Int. Cl.
*G01N 15/02* (2006.01)
*G01N 15/10* (2006.01)
*G01N 15/14* (2006.01)

(52) U.S. Cl.
CPC ......... *G01N 15/0227* (2013.01); *G01N 15/02* (2013.01); *G01N 15/10* (2013.01); *G01N 15/14* (2013.01); *G01N 15/1429* (2013.01)

(58) Field of Classification Search
None
See application file for complete search history.

(56) References Cited

U.S. PATENT DOCUMENTS

| 4,866,639 A * | 9/1989 | Adrian ..................... G01P 5/001 356/28 |
| 2007/0229823 A1* | 10/2007 | Sung .................. G01N 15/1463 356/336 |
| 2017/0074768 A1* | 3/2017 | Moitzi ............... G01N 15/0227 |
| 2018/0031464 A1* | 2/2018 | Norisuye ............. G01N 29/024 |

FOREIGN PATENT DOCUMENTS

| JP | H07-049302 A | 2/1995 |
| JP | 2008-261737 A | 10/2008 |
| JP | 2010-060544 A | 3/2010 |

OTHER PUBLICATIONS

Tafvizi, Anahita, et al. "Tumor suppressor p53 slides on DNA with low friction and high stability." Biophysical journal 95.1 (2008): L01-L03. (Year: 2008).*
International Preliminary Report on Patentability and Written Opinion issued in PCT/JP2016/060479 dated Oct. 3, 2017.
International Search Report issued in PCT/JP2016/060479; dated Jun. 7, 2016.

(Continued)

*Primary Examiner* — Shawn Decenzo
(74) *Attorney, Agent, or Firm* — Studebaker & Brackett PC

(57) ABSTRACT

To provide a particle size measuring device that enables simple in-line measurement of the particle size even in a case of nano-sized particles during dispersion. Provided is a particle size measuring device which measures the particle size of particles that perform Brownian motion in a disper- (Continued)

sion medium. The particle size measuring device includes a transparent column which accommodates a dispersion medium therein; a laser light irradiating unit which irradiates the dispersion medium in the column with laser light; an imaging unit which includes a camera that images the dispersion medium in the column; an image analyzing unit which acquires a displacement of corresponding particles from at least a plurality of images captured at a predetermined time interval $\Delta t$; and a calculating unit which calculates the particle size based on the fact that a root mean square value of the displacement is proportional to $k_B T/3\pi\eta d$ where $k_B$ represents a Boltzmann constant, T represents an absolute temperature, $\eta$ represents a viscosity coefficient of the dispersion medium, and d represents the particle size.

6 Claims, 7 Drawing Sheets

(56) References Cited

OTHER PUBLICATIONS

Rebecca A. Dragovic et al.; "Sizing and Phenotyping of Cellular Vesicles Using Nanoparticle Tracking Analysis"; Nanomedicine: Nanotechnology, Biology, and Medicine; Dec. 2011; pp. 780-788; vol. 7, Issue 6.

R.A. Dragovic et al., "Sizing and phenotyping of cellular vesicles using Nanoparticle Tracking Analysis", Nanomedicine: Nanotechnology, Biology, and Medicine, vol. 7, No. 6, Dec. 1, 2011, pp. 780-788.

* cited by examiner

| | ROOT MEAN SQUARE VALUE OF TRANSITIONAL DISPLACEMENT (AVERAGE VALUE) $m^2S^{-1}$ | PARTICLE SIZE CALCULATED FROM TRANSITIONAL DISPLACEMENT (AVERAGE VALUE) nm |
|---|---|---|
| X | $5.77 \times 10^{-12}$ | 337 |
| Y | $6.41 \times 10^{-12}$ | |

FIG. 8

| | ROOT MEAN SQUARE VALUE OF TRANSITIONAL DISPLACEMENT $m^2 S^{-1}$ | PARTICLE SIZE CALCULATED FROM TRANSITIONAL DISPLACEMENT (AVERAGE VALUE) nm |
|---|---|---|
| X | $7.98 \times 10^{-12}$ | 321 |
| Y | $7.98 \times 10^{-12}$ | |

FIG. 9

| sample name | material | commercial name | maker | official diameter / nm | density / g cm⁻³ |
|---|---|---|---|---|---|
| P100 | polystyrene latex | STADEX SC-0100-D | JSR Corporation | 100 | 1.06 |
| P300 | | STADEX SC-032-S | JSR Corporation | 309 | 1.05 |
| S100 | silica | Silica Microspheres, Cat#24041 | Polysciences, Inc | 100 | 2.00 |
| S300 | | Silica Microspheres, Cat#24321 | Polysciences, Inc | 300 | 2.00 |
| G100 | gold | Concentrated Accurate Spherical Gold Nanoparticles, A11C-100-NPC | NANO PARTZ Inc. | 100 | 19.30 |

PARTICLE SIZE MEASURING METHOD AND DEVICE

TECHNICAL FIELD

The present invention relates to a particle size measuring method and a particle size measuring device for measuring the particle size of particles in a dispersion medium and particularly relates to a particle size measuring method and a particle size measuring device which enable measurement of the particle size even in a case of nano-sized particles.

BACKGROUND ART

Various methods of optically measuring the particle size of particles in a dispersion medium have been suggested. For example, in a process of producing nano-sized particles used for a resist or the like of a semiconductor, that is, in a process of synthesizing a so-called "nano material", the particle size of obtained particles is measured in order to control the quality of the particles.

For example, Patent Document 1 discloses a batch type method of measuring particle size distribution of nano-sized particles through sampling. First, a dispersion liquid is obtained by dispersing a particle group with known particle size distribution in a dispersion medium used for measurement, and then the dispersion liquid is allowed to stand. Further, the temporal change in the number of photons is measured by irradiating the dispersion liquid with laser light and detecting scattered light from the particle group using light detecting means. The mobility and the fluctuation rate of the particle group are obtained by data processing means based on the Brownian motion of the particle group to be measured and the force applied to the particles is calculated to obtain the correlation between the fluid shear stress and the fluid shear rate of the dispersion medium on the surface of the particles. Next, the particle size distribution of a particle group whose particle size distribution is unknown is determined in order to satisfy the correlation between the fluid shear stress and the fluid shear rate which have been previously acquired in the same manner as described above.

Batch type measurement through sampling has been performed as the method disclosed in Patent Document 1, but it is desired that the particle size of particles in a flowing dispersion medium is able to be simply measured by not performing an in situ measurement but an in-line measurement because a measurement time is also required. Further, a particle counter has been mainly used in in-line particle size measurement, and a so-called particle size in terms of polystyrene latex calibrated with a standard substance such as polystyrene latex is used in the particle counter. However, it is desired that the particle size to be measured is not the particle size in terms of polystyrene latex and standard substance calibration is not required. A device that performs measurement on particles having a particle size larger than the nano size has been suggested as such an in-line particle size measuring device.

For example, Patent Document 2 discloses a particle size measuring device which measures the particle size of particles of the order of micron in a dispersion medium flowing in a channel at a predetermined speed. In such a device, particles in a dispersion medium are photographed and the particle size thereof is measured from the obtained image data. Particularly, since the apparent particle size varies depending on the difference in photographing distance, the apparent particle size is corrected by obtaining the flow rate of measured dispersion medium, a position in a direction perpendicular to a photographing direction and a flow direction, and the speed of particles in the flow direction from the image data, and calculating the position of particles in the photographing direction based on the Navier-Stokes equation.

Further, Patent Document 3 discloses a particle size measuring device which performs measurement by using focused light beams focused at a focal point with a condensing lens in measurement of the particle size of particles of the order of submicron in a dispersion liquid flowing in a channel at a predetermined speed. Since the focused light beams applied to the dispersion liquid are optically changed by the particles, the change is measured to acquire the particle size correlated with the change. Further, since the optical change varies depending on a distance from a light source to a passing position of the particles, the optical change is corrected by the passing position of the particles. The passing position of the particles is able to be calculated using the time taken for the particles to pass through the focused light spreading from the focal point.

CITATION LIST

Patent Document

Patent Document 1: Japanese Patent Application Laid-Open No. 2010-060544
Patent Document 2: Japanese Patent Application Laid-Open No. 2008-261737
Patent Document 3: Japanese Patent Application Laid-Open No. 7-049302

SUMMARY

Technical Problem

In order to simply measure the particle size, it is desired that the particle size is able to be measured without requiring standard substance calibration. Further, in the production line of nano-sized particles, it is also desired that the particle size is able to be simply measured by in-line measurement.

The present invention has been made in consideration of the above-described circumstances, and an object thereof is to provide a particle size measuring device and a particle size measuring method that enable simple measurement of the particle size of dispersed particles even in a case of nano-sized particles.

Solution to Problem

As a result of intensive research conducted by the present inventors in order to solve the above-described problems, it was found that the particle size is able to be calculated from a displacement resulting from Brownian motion and even the particle size of nano-sized particles is able to be calculated in a case of particles that perform Brownian motion in the line, thereby completing the present invention.

According to an aspect of the present invention, there is provided a particle size measuring device which measures the particle size of particles that perform Brownian motion in a dispersion medium, the device comprising: a transparent column which accommodates a dispersion medium therein; a laser light irradiating unit which irradiates the dispersion medium in the column with laser light; an imaging unit which includes a camera that images the dispersion medium in the column; an image analyzing unit which acquires a displacement of corresponding particles from at least a plurality of images captured at a predetermined time interval Δt; and a calculating unit which calculates the particle size based on the fact that a root mean square value of the displacement is proportional to $k_B T/3\pi\eta d$ where $k_B$ represents a Boltzmann constant, T represents an absolute temperature, η represents a viscosity coefficient of the dispersion medium, and d represents the particle size.

According to the present invention, it is possible to measure the particle size of particles that perform Brownian motion in the line even in a case where the particles are nano-sized particles.

In the invention described above, the image analyzing unit may obtain a scattered light intensity and a number concentration of a plurality of the particles from the images, and the calculating unit may determine a material of the particles by acquiring a relative refractive index m using a relational expression between a scattered light intensity I which is the intensity of the scattered light and an incident light intensity $I_0$ which is the intensity of the laser light and performing absorption correction, where c represents the number concentration, r represents the distance between the particles and the camera, λ represents a wavelength of the laser light, d represents the particle size, and m represents a relative refractive index of the particles with respect to the dispersion medium. According to the present invention, it is possible to measure the particle size of the particles in the line and determine the material of such particles.

$$I \propto I_0 \frac{c}{2r^2}\left(\frac{2\pi}{\lambda}\right)^4\left(\frac{d}{2}\right)^6\left|\frac{m^2-1}{m^2+2}\right|^2$$

In the invention described above, the dispersion medium may be allowed to flow along an axis line in the column, an optical axis of the camera may be disposed toward a direction perpendicular to the axis line, and the image analyzing unit may further acquire the displacement by subtracting a moving component due to a flow velocity of the dispersion medium from a moving component in a direction along the axis line of the particles in the images. According to the present invention, it is possible to measure the particle size even in a case where the dispersion medium in the line flows.

In the invention described above, the image analyzing unit may further acquire a moving component in a vertical direction and a moving component in a horizontal direction of the corresponding particles in the images, and the calculating unit may calculate the particle size of only the corresponding particles in which a difference or a ratio between the root mean square value of the moving component in the vertical direction and the root mean square value of the moving component in the horizontal direction is set to be in a predetermined range. According to the invention, even in a case where the dispersion medium contains a plurality of types of particles having different densities which are expected to have fallen or floated due to gravity, it is possible to measure the particle size of only the particles that are of a type having a density which is in a constant relationship with the density of the dispersion medium.

According to another aspect of the present invention, there is also provided a particle size measuring method of measuring the particle size of particles that perform Brownian motion in a dispersion medium of a column, the method comprising: a step of imaging the dispersion medium in the column by an imaging unit which includes a camera while irradiating inside the column with laser light; an image analyzing step of acquiring a displacement of corresponding particles from at least a plurality of images captured at a predetermined time interval Δt; and a calculating step of calculating the particle size based on the fact that $k_B T/3\pi\eta d$ is proportional to a root mean square value of the displacement where $k_B$ represents a Boltzmann constant, T represents an absolute temperature, η represents a viscosity coefficient of the dispersion medium, and d represents the particle size.

According to the present invention, it is possible to measure the particle size of particles that perform Brownian motion in the line even in a case where the particles are nano-sized particles.

In the invention described above, the image analyzing step may further include a step of obtaining a scattered light intensity and a number concentration of a plurality of the particles from the images, and the calculating step may further include a step of determining a material of the particles by acquiring a relative refractive index m using a relational expression between a scattered light intensity I which is the intensity of the scattered light and an incident light intensity $I_0$ which is the intensity of the laser light and performing absorption correction, where c represents the number concentration, r represents the distance between the particles and the camera, λ represents a wavelength of the laser light, d represents the particle size, and m represents a relative refractive index of the particles with respect to the dispersion medium. According to the present invention, it is possible to measure the particle size of the particles in the line and determine the material of such particles.

$$I \propto I_0 \frac{c}{2r^2}\left(\frac{2\pi}{\lambda}\right)^4\left(\frac{d}{2}\right)^6\left|\frac{m^2-1}{m^2+2}\right|^2$$

In the invention described above, the dispersion medium may be allowed to flow along an axis line in the column, an optical axis of the camera may be disposed toward a direction perpendicular to the axis line, and the displacement may be acquired by subtracting a moving component due to a flow velocity of the dispersion medium from a moving component in a direction along the axis line of the particles in the images in the image analyzing step. According to the present invention, it is possible to measure the particle size even in a case where the dispersion medium in the line flows.

In the invention described above, a moving component in a vertical direction and a moving component in a horizontal direction of the corresponding particles in the images may be acquired in the image analyzing step, and the particle size of only the corresponding particles in which a difference or a ratio between the root mean square value of the moving component in the vertical direction and the root mean square value of the moving component in the horizontal direction is set to be in a predetermined range may be calculated in the calculating step. According to the invention, even in a case where the dispersion medium contains a plurality of types of particles having different densities which are expected to have fallen or floated in the dispersion medium due to gravity, it is possible to measure the particle size of only the particles that are of a type having a density which is in a constant relationship with the density of the dispersion medium.

BRIEF DESCRIPTION OF DRAWINGS

FIG. 8 shows an example of measuring the particle size of polystyrene latex particles.

FIG. 9 is a table illustrating particles used for measurement of moving components.

DESCRIPTION OF EMBODIMENTS

Hereinafter, a particle size measuring device and a particle size measuring method which are examples of the present invention will be described in detail.

[Particle Size Measuring Device]

Figure 1:
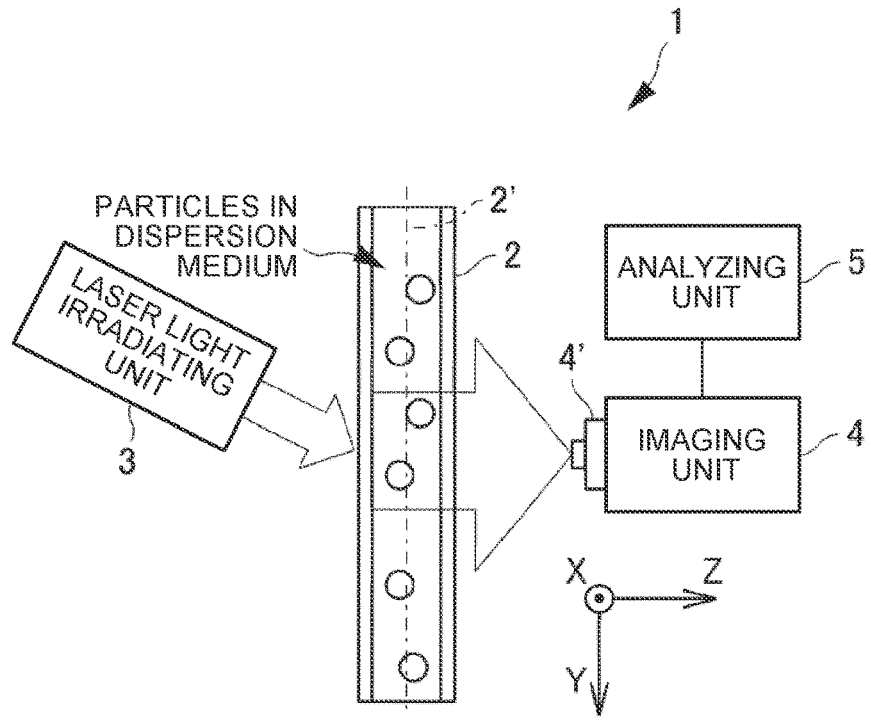
FIG. 1 is a block diagram illustrating main parts of a particle size measuring device according to the present invention.

As illustrated in FIG. 1, a particle size measuring device 1 includes a transparent column 2 which is capable of accommodating a dispersion medium, in which particles are dispersed, therein; a laser light irradiating unit 3 which is capable of irradiating the particles in the column 2 with laser light; an imaging unit 4 which includes a camera 4' that images the inside of the column 2; an analyzing unit 5 which analyzes the image obtained by the imaging unit 4 and calculates the particle size. The details of the column 2 will be described later. Here, an X axis, a Y axis, and a Z axis are determined such that the X axis is along the horizontal direction and the Y axis is along the vertical direction and is directed downward.

The laser light irradiating unit 3 is disposed such that scattered light from particles in the dispersion medium is easily imaged by the camera 4', that is, the intensity of scattered light is able to be measured more strongly, and according to the present embodiment, an optical axis of laser light to be emitted is inclined with respect to an axis line 2' of the column 2. Particularly, in order to image one particle with high precision using scattered light, it is preferable that the intensity of scattered light is able to be measured more strongly using laser light having a short wavelength or laser light having a high intensity such that the sensitivity of the camera 4' increases.

The camera 4' of the imaging unit 4 is capable of continuously imaging the dispersion medium in the column 2 in the Z axis direction perpendicular to the axis line 2' of the column 2 at a predetermined time interval Δt. In other words, the optical axis of the camera 4' is disposed vertically to the axis line 2' so that an image on an X-Y plane in parallel with the axis line 2' is able to be imaged as a moving image. The captured image is recorded as a moving image in which each predetermined time interval Δt corresponds to one frame. As the camera 4', a microscope camera, a CCD camera, a CMOS, or the like is able to be used. It is preferable that the camera 4' is set such that an image of particles in the dispersion medium to be imaged by scattered light is sufficiently brightened by, for example, lengthening the shutter time according to the range of the particle size of particles to be measured. At this time, the shutter time to be set is required not to exceed the predetermined time interval Δt (the time corresponding to one frame as a moving image).

The analyzing unit 5 is connected to the imaging unit 4 and performs image analysis and calculation on a captured image. The particle size is measured by the image analysis and the calculation, and the material of particles is determined. The details thereof will be described later.

[Measurement Method 1: When Dispersion Medium has Flow Velocity in Column (In-Line Measurement)]

Next, a method of measuring the particle size when the dispersion medium in the column 2 has a flow velocity will be described using FIG. 2 with reference to FIGS. 1 and 3.

In the particle size measuring device 1 illustrated in FIG. 1, the column 2 is a channel that allows the dispersion medium, in which particles are dispersed, to pass therethrough along the axis line 2'. Further, the directions of the X axis and the Y axis with respect to the gravity direction have been described, but the direction of each axis with respect to the gravity direction is able to be arbitrarily determined.

Figure 2:
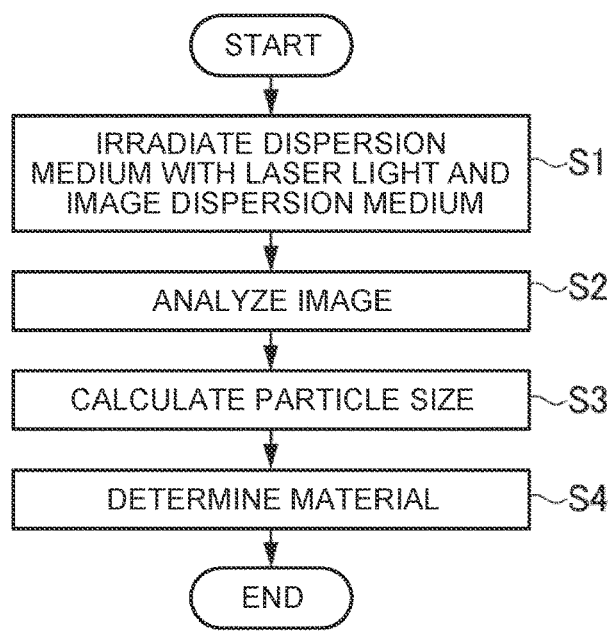
FIG. 2 is a flowchart illustrating a particle size measuring method according to the present invention.
Figure 3:
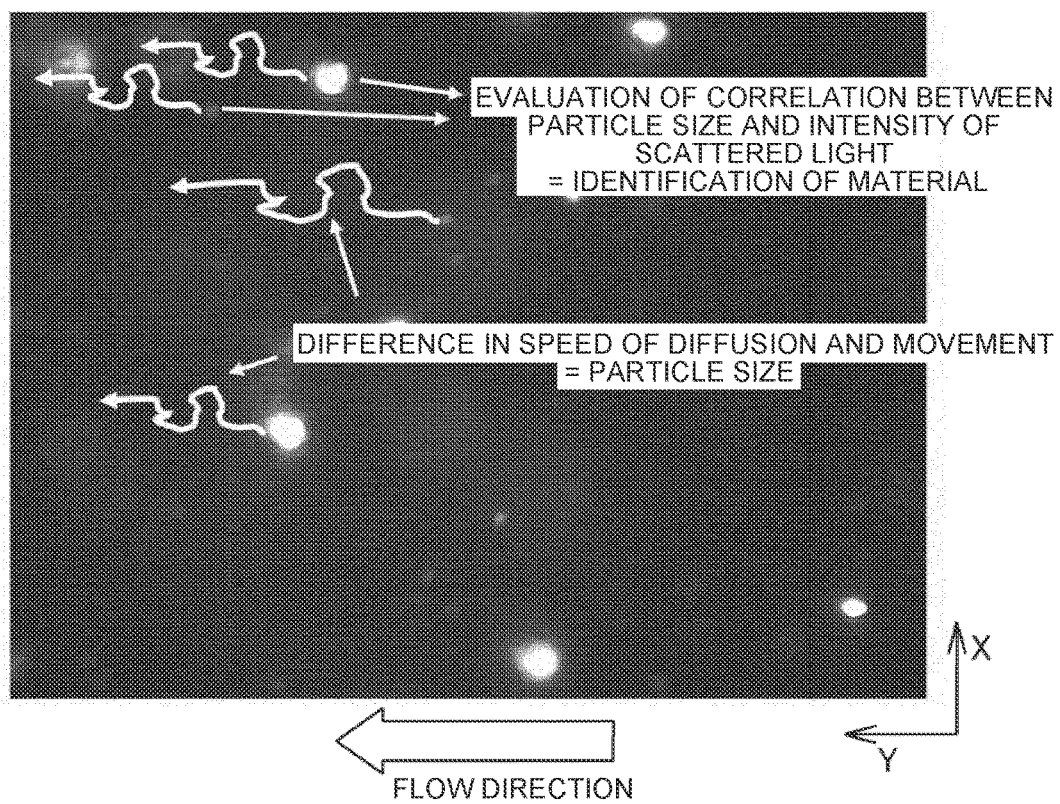
FIG. 3 is a diagram illustrating imaged particles in a dispersion medium.

Referring to FIG. 2 together with FIG. 1, first, the dispersion medium in which particles to be measured are dispersed is allowed to pass through the column 2 along the axis line 2' in the particle size measuring device 1. Here, the shape of the column 2 and the viscosity or the flow velocity of the dispersion medium are adjusted in order to make the flow of the dispersion medium into laminar flow. Thereafter, the dispersion medium in the column 2 is irradiated with laser light using the laser light irradiating unit 3 and the dispersion medium is imaged by the camera 4' (S1). At this time, images obtained in the above-described manner are made into a series of images captured at a predetermined time interval Δt, that is, a moving image. Respective images are formed of images on the X-Y plane including the Y axis in parallel with the axis line 2' of the column 2 in the flow direction of the dispersion medium. In other words, the Y axis in parallel with the flow direction and the X axis perpendicular to the Y axis are able to be set on a captured image as illustrated in FIG. 3.

Next, image analysis is performed (S2). In the image analysis, in each of the images, a position of a particle corresponding to one particle is acquired from an image and then a position of the corresponding particle which is separated from the obtained position by the time interval Δt is acquired from the next image. A displacement of the corresponding particle between two images is acquired based on a difference between the positions. The method of acquiring the displacement will be described later in detail. This operation is performed on each of a series of images. Further, in order to determine the material (S4) described later, the intensity of scattered light in the corresponding particle on an image is measured and recorded, the number of images of particles in a predetermined range is counted, and the number concentration of the particles is calculated. In addition, the number concentration may be measured using a particle counter.

Next, the particle size is calculated (S3). The particle size is calculated based on the fact that the root mean square value of the acquired displacement is proportional to a diffusion coefficient D. The diffusion coefficient D satisfies the following Stokes-Einstein equation where $k_B$ represents a Boltzmann constant, T represents an absolute temperature, $\eta$ represents a viscosity coefficient of the dispersion medium, and d represents the particle size.

$$D = k_B T / 3\pi\eta d$$

In other words, the above-described root mean square value of the displacement is proportional to the right side of the equation. The particle size corresponding to the measured displacement resulting from the diffusion of the corresponding particles is able to be calculated using the relationship. The method of calculating the particle size will be described later in detail.

In addition, the material of particles whose particle size has been calculated is determined (S4).

As described above, the analyzing unit 5 records the intensities of scattered light from each corresponding particle on the images. In a case where the calculated particle size is sufficiently small with respect to the wavelength of laser light which is incident light, that is, in a case of Rayleigh scattering, the following expression is satisfied.

$$I \propto I_0 \frac{c}{2r^2} \left(\frac{2\pi}{\lambda}\right)^4 \left(\frac{d}{2}\right)^6 \left|\frac{m^2-1}{m^2+2}\right|^2$$

In this expression, c represents the number concentration of particles, r represents the distance between the particles and the camera 4', λ represents a wavelength of incident light, I represents the intensity of scattered light, $I_0$ represents the intensity of incident light, d represents the particle size of the corresponding particles, and m represents the relative refractive index of the particles with respect to the dispersion medium. Accordingly, m varies when the materials of particles are different even when the particles have the same particle size. In other words, the relative refractive index m is able to be acquired from the changing distance r from one particle to the camera 4' and the intensity I of scattered light. The determination of the material is able to be performed along with the measurement of the particle size by correcting the relative refractive index m with the imaginary term of absorption and referring to known refractive indices listed in Table 1 based on the absorption correction. In addition, r is able to be actually measured or is able to be inversely calculated and evaluated based on the particle size and samples known for the Rayleigh ratio.

TABLE 1

| Substance name | Refractive index | Intensity of scattered light (relative value with respect to gas) |
|---|---|---|
| SiO2 | 1.44 | 0.10 |
| Au | 0.34 | 7.13 |
| Ag | 0.17 | 8.29 |
| air | 1.00 | 1.00 |
| PSL | 1.61 | 0.63 |
| PMMAL | 1.73 | 1.22 |
| TiO2 | 2.50 | 7.30 |
| Al2O3 | 1.81 | 1.70 |
| C | 2.00 | 3.05 |

Meanwhile, in measurement of the particle size, since the diffusion of particles is affected by the flow in in-line measurement, it becomes difficult to precisely calculate the particle size from the distance of movement due to the diffusion. Here, in the present embodiment, the particle size is calculated by acquiring the displacement so as not to be affected by the flow as described below.

Hereinafter, the method of acquiring the displacement of the corresponding particles in the image analysis (S2) described above and the method of calculating the particle size (S3) will be described. In the calculation of the particle size, two different cases of using a one-dimensional diffusion coefficient and a two-dimensional diffusion coefficient will be described.

(1) Case of Using One-Dimensional Diffusion Coefficient

In the image analysis (S2), the Y axis in parallel with the flow direction of the dispersion medium and the X axis perpendicular to the Y axis are able to be set on respective images as described above. Here, the displacement is not affected by the flow of the dispersion medium by obtaining the displacement only by using a moving component δx in parallel with the X axis. As described above, the moving component δx is acquired in each of a series of images.

In the calculation of the particle size (S3), a diffusion coefficient $D_1$ is acquired by [(δx)$^2$] which is a root mean square value of the acquired moving component δx. Here, in the movement of fine particles such as nano-sized particles due to the Brownian motion, particles isotropically move in all directions of the X axis, the Y axis, and the Z axis. When it is assumed that the movement is not affected by the flow of the dispersion medium or the gravity described below, the root mean square values of the moving component are the same in all directions in a case where the trajectory of the corresponding particles is traced on the images for a sufficient time. Therefore, [(δx)$^2$] is able to be used as a root mean square value of the one-dimensional displacement and then the one-dimensional diffusion coefficient is able to be acquired. In other words, the one-dimensional diffusion coefficient $D_1$ is calculated by the following equation.

$$[(\delta x)^2] = 2D_1 \Delta t$$

Further, when $k_B$ represents a Boltzmann constant, T represents an absolute temperature, η represents a viscosity coefficient of the dispersion medium, and d represents the particle size, the particle size is calculated using the following Stokes-Einstein equation.

$$D_1 = k_B T / 3\pi \eta d$$

In this manner, in the analysis of a series of images, the one-dimensional displacement is obtained from the one-dimensional moving component so as not to be affected by the flow of the dispersion medium and the particle size of the one corresponding particle is able to be calculated based on the displacement.

(2) Case of Using Two-Dimensional Diffusion Coefficient

In the same manner as described above, the Y axis in parallel with the flow direction of the dispersion medium and the X axis perpendicular to the Y axis are able to be set on respective images. Here, the displacement is obtained by a moving component δx in parallel with the X axis and a moving component δy in parallel with the Y axis. The moving component δy is obtained by correcting the amount of movement due to the flow on images. In other words, an amount obtained by multiplying the flow velocity of the dispersion medium by Δt is subtracted from the movement amount in the Y axis direction on images to obtain the moving component δy. In this manner, the moving component δx and the moving component δy are not affected by the flow of the dispersion medium. In each of a series of images, the moving component δx and the moving component δy are acquired. In this case, the flow velocity of the dispersion medium is obtained by mounting a flow rate sensor on the column 2.

In the calculation of the particle size (S3), a diffusion coefficient $D_2$ is acquired by [(δx)$^2$] which is a root mean square value of the acquired moving component δx and [(δy)$^2$] which is a root mean square value of the acquired moving component δy. As described above, since the root mean square values of the moving components are the same in all directions in a case where the trajectory of the corresponding particles is traced on images for a sufficient time, $[(\delta x)^2]+[(\delta y)^2]$ is able to be used as a root mean square value of the two-dimensional displacement and then the two-dimensional diffusion coefficient is able to be acquired. In other words, the two-dimensional diffusion coefficient $D_2$ is calculated by the following equation.

$$[(\delta x)^2]+[(\delta y)^2]=4D_2\Delta t$$

Further, when $k_B$ represents a Boltzmann constant, T represents an absolute temperature, η represents a viscosity coefficient of the dispersion medium, and d represents the particle size, the particle size is calculated using the following Stokes-Einstein equation.

$$D_2=k_B T/3\pi\eta d$$

In this manner, in the analysis of a series of images, the two-dimensional displacement is obtained from the two-dimensional moving component so as not to be affected by the flow of the dispersion medium and the particle size of the one corresponding particle is able to be calculated based on the displacement.

Further, since the particle size is evaluated as a function of the intensity of scattered light in a conventional particle counter that is used for typical in-line measurement of the particle size, the detection angle of scattered light needs to be fixed to a constant angle, and thus the intensity of detected light is frequently insufficient in small particles such as nano-sized particles. On the contrary, since the particle size is able to be calculated from the movement based on diffusion according to the above-described method, there is almost no need for control of the detection angle of scattered light and scattering is able to be accumulated in a wide scattering angle range. Accordingly, the intensity of detected scattered light is able to be sufficiently obtained even in a case of nano-sized particles and then the particle size is able to be measured. For example, the intensity of scattered light may be increased using a plurality of laser light irradiating units 3.

According to the above-described method, it is possible to easily perform measurement of the particle size of particles in the dispersion medium and identification of the material of particles in a short time and various applications of the method such as monitoring the material synthesis line, controlling the quality of particles, identifying bubbles and particles in the production line which has not been possible when using a particle counter, and evaluating impurity contamination in the preparation production line are able to be expected.

Measurement Example 1

An example of measuring the particle size of polystyrene latex particles will be described with reference to FIG. 4.

The particle size of polystyrene latex particles (diameter of approximately 100 nm) is measured by circulating a dispersion liquid obtained by dispersing the particles therein into the column 2 using ultrapure water as the dispersion medium. The measured particle size (diameter) and the number distribution thereof are illustrated in FIG. 4.

Figure 4:
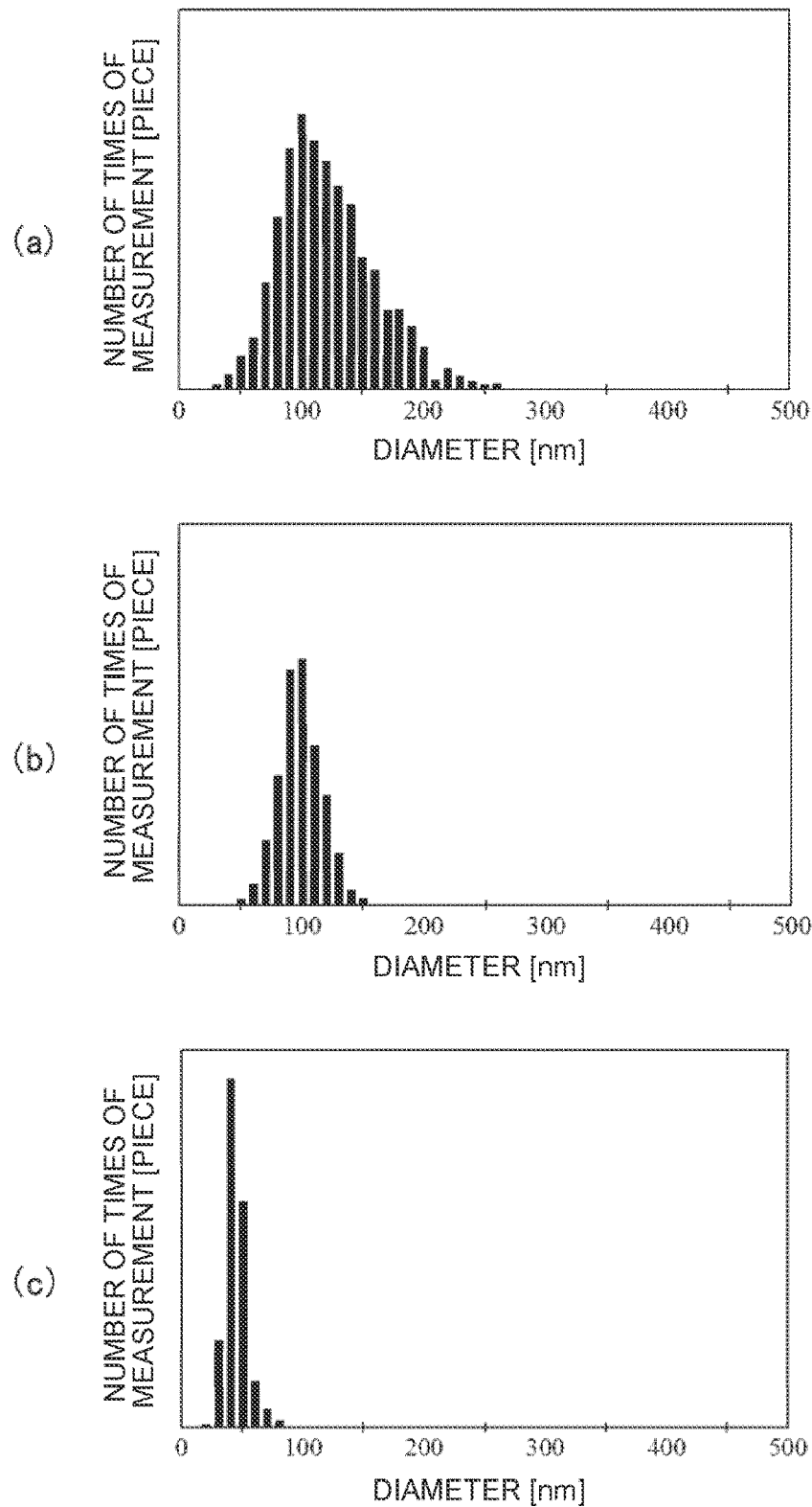
FIG. 4 shows an example of measuring the particle size of polystyrene latex.

Here, the measurement results in a case of using a one-dimensional diffusion coefficient are illustrated in FIG. 4(*a*). Further, the measurement results in a case of using a two-dimensional diffusion coefficient are illustrated in FIG. 4(*b*). The measurement results in a case where the amount of movement due to the flow on images has not been corrected in an example of using the two-dimensional diffusion coefficient for comparison are illustrated in FIG. 4(*c*).

As illustrated in FIGS. 4(*a*) and (*b*), in both cases of using the one-dimensional diffusion coefficient and the two-dimensional diffusion coefficient, distribution centering on the particle size of 100 nm is measured. Meanwhile, the variation width thereof is small in the case of using the two-dimensional diffusion coefficient. It is considered that the variation width is greatly affected by the state of the flow of the dispersion medium in the column 2, particularly, whether the state of the flow is laminar flow. Further, as illustrated in FIG. 4(*c*), an error of the particle size to be measured is able to be reduced by performing correction of subtracting the amount of movement due to the flow.

Measurement Example 2

Along with the measurement of the particle size of various particles, an example of determining materials of the particles will be described with reference to FIG. 5.

With respect to silica particles s (silica), polystyrene latex particles p (PSL), gold particles g (gold) which have the same particle size, the particle size is measured according to the above-described measurement method and the intensity of scattered light is acquired. The results thereof are listed in FIG. 5.

Figure 5:
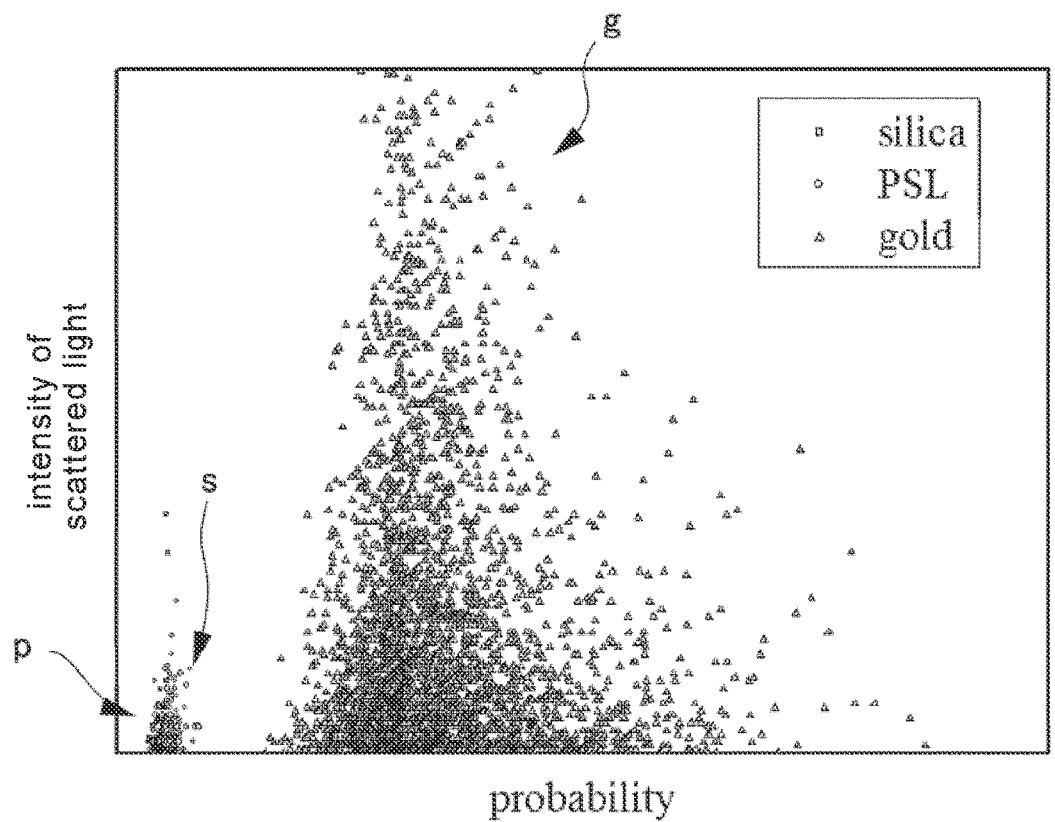
FIG. 5 shows an example of measuring the scattered light intensities of three types of particles.

As illustrated in FIG. 5, in the intensities of scattered light of the silica particles s, the polystyrene latex particles p, and the gold particles g, the distributions are partially overlapped, but the intensities of scattered light are different. In other words, the determination of materials of the particles is able to be performed by referring to known refractive indices.

[Measurement Method 2: When Dispersion Medium does not have Flow Velocity in Column (Batch Measurement)]

Next, a method of measuring the particle size when the dispersion medium in the column 2 does not have a flow velocity will be described using FIG. 2 with reference to FIGS. 1 and 6. Here, a cellular column formed by closing the top and the bottom is used as the column 2.

Here, the particle size is measured by selecting particles to be measured based on the influence of a difference in density between particles and the dispersion medium in which the particles are dispersed on the Brownian motion in the image analysis (S2) and the calculation (S3) of the particle size illustrated in FIG. 2. The method of selecting such particles will be described.

In the Brownian motion, particles isotropically move in all directions of the X axis, the Y axis, and the Z axis, but the movement in the Y axis direction (vertical direction) is affected by the gravity and particles equivalently move at least in the X axis direction and the Z axis direction. Consequently, in the case where the trajectory of the corresponding particles is traced on images for a sufficient time, the root mean square values of the moving component δx in the X axis direction and the moving component δz in the Z axis direction are the same as each other.

Here, attention is focused on a difference or a ratio between the root mean square value $[(\delta x)^2]$ of the moving component δx in the horizontal direction and the root mean square value $[(\delta y)^2]$ of the moving component δy in the vertical direction. The particle size is calculated (S3) by selecting particles, in which the difference or the ratio therebetween is in a constant range, from a series of images and performing the above-described process on the selected particles.

Figures 6, 7:
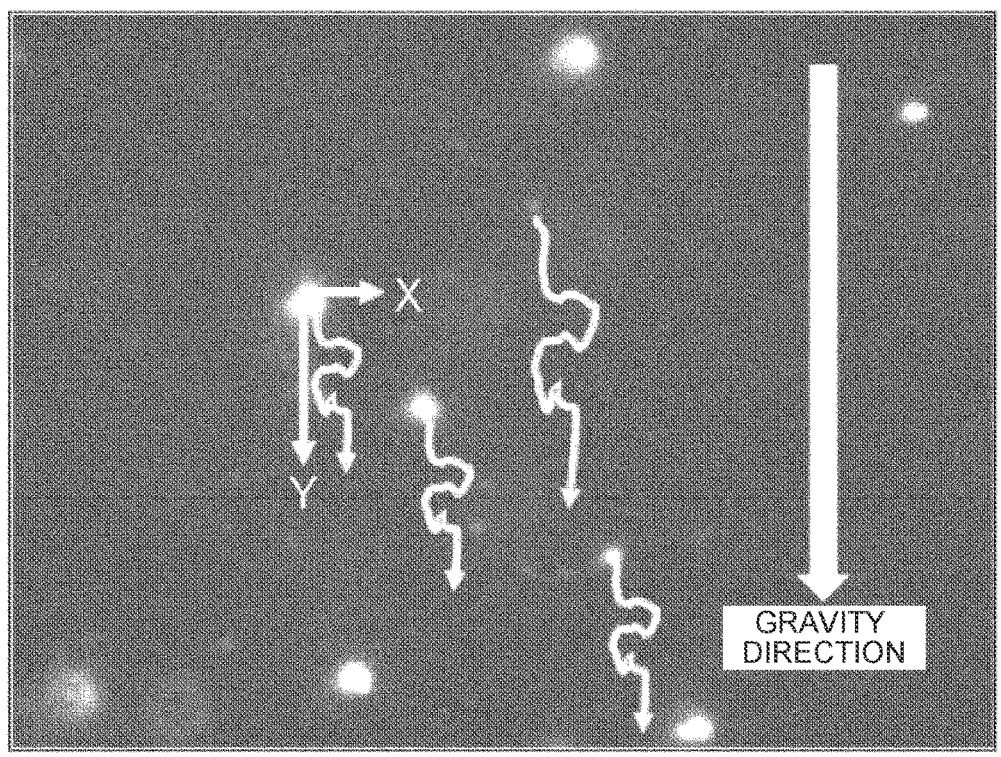
FIG. 6 is a diagram illustrating imaged particles in a dispersion medium.
FIG. 7 shows an example of measuring the particle size of silica particles.

As described above, the Brownian motion of fine particles has isotropy, but the particles in the Y axis direction which is the vertical direction are affected by the gravity as illustrated in FIG. 6. Therefore, the root mean square value $[(\delta y)^2]$ of the moving component $\delta y$ in the Y axis direction changes in response to a difference in density (specific gravity) between the particles and the dispersion medium. In other words, in $[(\delta y)^2]$ and the root mean square value $[(\delta x)^2]$ of the moving component in the horizontal direction, when the density of the dispersion medium and the density of the particles are the same as each other, "$[(\delta x)^2]=[(\delta y)^2]$" is satisfied. Further, when the density of the dispersion medium and the density of the particles are different from each other, "$[(\delta x)^2]<[(\delta y)^2]$" is satisfied. In other words, particles having the same density, that is, particles formed of the same material are able to be selected based on the difference or the ratio between $[(\delta x)^2]$ and $[(\delta y)^2]$. The average value of $\delta y$ becomes positive (directed downward in FIG. 6) in a case where the density of particles is greater than the density of the dispersion medium, and the average value of $\delta y$ becomes negative (directed upward in FIG. 6) in a case where the density of particles is smaller than the density of the dispersion medium, and particles are able to be selected based on this. Further, particles having a specific density are able to be selected by using one or a plurality of types of dispersion mediums having different densities.

The Y axis is not necessarily along the vertical direction since it is sufficient that the movement of particles that are affected by the difference in density between the particles and the dispersion medium is able to be measured. Accordingly, the Y axis may have an inclination with respect to the horizontal direction. That is, preferably, the optical axis of the camera 4' is along the horizontal direction and it is sufficient that the optical axis has an inclination with respect to the vertical direction.

Here, the material of nano-sized particles to be measured is a nano material having an average particle size of 10 to 1500 nm, and examples thereof include silica, polystyrene latex, and carbon black. Further, the target for measurement is not limited to nano-sized particles, and fine particles in which the Brownian motion is able to be observed are able to be measured.

According to the above-described method, particles to be measured are selected based on the difference in density and then the particle size is able to be measured. In other words, when particles to be measured are selected and then the particle size thereof is acquired, for example, only the particle size of bubbles contained in the dispersion medium from which impurities are excluded is able to be correctly measured. Specifically, it has been known that growth of plants is able to be promoted by allowing a nutrient solution to contain bubbles in a plant factory, and the particle size thereof is able to be measured for the purpose of quality control on the size of bubbles contained in the nutrient solution. In other words, the nutrient solution contains a large amount of impurities and only the particle size of bubbles contained therein from which the impurities are excluded is able to be correctly measured.

Measurement Example 1

An example of measuring the particle size of silica particles will be described with reference to FIG. 7.

Silica particles (approximately 300 nm: manufactured by Polysciences, Inc., product name: Microspheres, catalog number: 24321, lot number: 603704, specific gravity: 2.00) are prepared so as to have a concentration of 0.0004 mg/mL using ultrapure water as the dispersion medium. The dispersion liquid is injected into the column 2 and the movement of the particles is measured according to the above-described method.

As illustrated in FIG. 7, in silica particles having a higher density (specific gravity) than that of water (ultrapure water), the root mean square value of the moving component $\delta x$ in the X axis direction and the root mean square value of the moving component $\delta y$ in the Y axis direction are different from each other. Accordingly, it is possible to at least determine that the particles are formed of a substance having a higher specific gravity than that of water even in a case where the material of particles is unknown. Further, the number of particles selected based on the expression "$[(\delta x)^2]\leq[(\delta y)^2]$" is 563, and the particle size of the particles is able to be measured with high precision and the average value of the particle size is 337 nm.

Measurement Example 2

In the same manner as described above, an example of measuring the particle size of polystyrene latex particles will be described with reference to FIG. 8.

Polystyrene latex particles (approximately 300 nm: manufactured by JSR CORPORATION, product name: SC032-S, lot number: 100928, specific gravity: 1.054) are prepared so as to have a concentration of 0.0002 mg/mL using ultrapure water as the dispersion medium. The dispersion liquid is injected into the column 2 and the movement of the particles is measured according to the above-described method. Further, silica particles (approximately 300 nm: manufactured by Polysciences, Inc., product name: Microspheres, catalog number: 24321, lot number: 603704, specific gravity: 2.00) are further added to be prepared so as to have a concentration of 0.0004 mg/mL, and the measurement is performed in the same manner as described above.

As illustrated in FIG. 8, in polystyrene latex particles having almost the same density (specific gravity) as that of water (ultrapure water), the root mean square value of the moving component $\delta x$ in the X axis direction and the root mean square value of the moving component $\delta y$ in the Y axis direction coincide with each other. Accordingly, it is possible to at least determine that the particles are formed of a substance having the same specific gravity as that of water even in a case where the material of particles is unknown. Further, the number of particles selected based on the expression "$[(\delta x)^2]=[(\delta y)^2]$" is 406, and the particle size of the particles is able to be measured with high precision and the average value of the particle size is 321 nm.

Further, even when a dispersion medium obtained by mixing silica and polystyrene latex is used, the particle size of each particle is able to be measured in the above-described manner.

Measurement Example 3

In the same manner as described above, an example of measuring the particle size of dispersed particles which have a different particle size and different densities, and an example of determining the material thereof will be described with reference to FIGS. 9 and 10. Here, results of measuring the root mean square values of moving components in the X axis direction and the Y axis direction, in other words, in the horizontal direction and the vertical direction will be described.

As illustrated in FIG. 9, samples used for the measurement are polystyrene latex (sample names: P100 and P300), silica (silicon dioxide, sample names: S100 and S300), and gold (sample name: G100). In the table, the official diameters are acquired by a dynamic light scattering (DLS) method or a transmission electron microscope (TEM). The samples are dispersed in a dispersion medium formed of ultrapure water, and the root mean square values of moving components in the X axis direction and the Y axis direction per second are acquired according to the above-described method. The results thereof are illustrated in FIG. 10.

Figure 10:
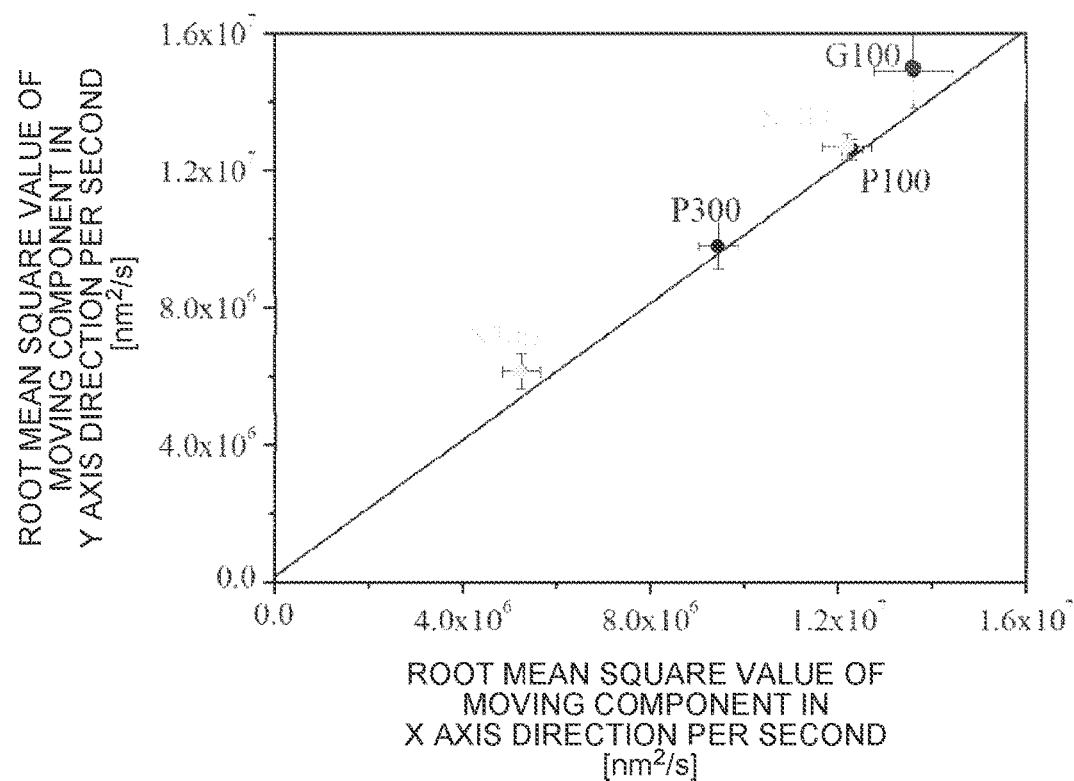
FIG. 10 shows an example of measuring the root mean square values of moving components in a horizontal direction and a vertical direction of particles having different densities per second.

As illustrated in FIG. 10, in the polystyrene latex (P100 and P300), the value of the Y axis direction is higher than the value of the X axis direction by approximately 1%, but the values of the X axis direction and the Y axis direction are almost the same as each other. On the contrary, in the silica and the gold, the values of the Y axis direction are clearly higher than the values of the X axis direction. In S100, S300, and G100, the values of the Y axis direction are higher than the values of the X axis direction respectively by 3%, 15%, and 10%. In other words, as described above, particles having the same density are able to be selected based on a difference or a ratio between the root mean square value $[(\delta x)^2]$ of the moving component in the horizontal direction and the root mean square value $[(\delta y)^2]$ of the moving component in the vertical direction. That is, the material of the particles is able to be determined. Further, each plot is an average value for 500 or more particles and is displayed by adding the standard deviation.

Hereinbefore, examples of the present invention and modified examples based on the examples have been described, but the present invention is not necessarily limited thereto. Various alternative examples and modified examples are able to be found by those skilled in the art without departing from the gist of the invention or the scope of the attached claims.

REFERENCE SIGNS LIST

1: particle size measuring device
2: column
3: laser light irradiating unit
4: imaging unit
4': camera
5: analyzing unit

What is claimed is:

1. A particle size measuring device which measures the particle size of particles that perform Brownian motion in a dispersion medium, the device comprising:
   a transparent column which accommodates a dispersion medium therein;
   a laser light irradiating unit which irradiates the dispersion medium in the column with laser light;
   an imaging unit which includes a camera that images the dispersion medium in the column;
   an image analyzing unit which acquires a displacement of corresponding particles from at least a plurality of images captured at a predetermined time interval $\Delta t$; and
   a calculating unit which calculates the particle size based on the fact that a root mean square value of the displacement is proportional to $k_B T/3\pi\eta d$ where $k_B$ represents a Boltzmann constant, T represents an absolute temperature, $\eta$ represents a viscosity coefficient of the dispersion medium, and d represents the particle size;
   wherein the image analyzing unit obtains a scattered light intensity and a number concentration of a plurality of the particles from the images, and
   the calculating unit determines a material of the particles by acquiring a relative refractive index m using a relational expression between a scattered light intensity I which is the intensity of the scattered light and an incident light intensity $I_0$ which is the intensity of the laser light and performing absorption correction, where c represents the number concentration, r represents the distance between the particles and the camera, $\lambda$ represents a wavelength of the laser light, d represents the particle size, and m represents a relative refractive index of the particles with respect to the dispersion medium:

$$I \propto I_0 \frac{c}{2r^2}\left(\frac{2\pi}{\lambda}\right)^4 \left(\frac{d}{2}\right)^6 \left|\frac{m^2-1}{m^2+2}\right|^2.$$

2. The particle size measuring device according to claim 1,
   wherein the dispersion medium is allowed to flow along an axis line in the column,
   an optical axis of the camera is disposed toward a direction perpendicular to the axis line, and
   the image analyzing unit further acquires the displacement by subtracting a moving component due to a flow velocity of the dispersion medium from a moving component in a direction along the axis line of the particles in the images.

3. The particle size measuring device according to claim 1,
   wherein the image analyzing unit further acquires a moving component in a vertical direction and a moving component in a horizontal direction of the corresponding particles in the images, and
   the calculating unit calculates the particle size of only the corresponding particles in which a difference or a ratio between the root mean square value of the moving component in the vertical direction and the root mean square value of the moving component in the horizontal direction is set to be in a predetermined range.

4. A particle size measuring method of measuring the particle size of particles that perform Brownian motion in a dispersion medium of a column, the method comprising:
   a step of imaging the dispersion medium in the column by an imaging unit which includes a camera while irradiating inside the column with laser light;
   an image analyzing step of acquiring a displacement of corresponding particles from at least a plurality of images captured at a predetermined time interval $\Delta t$; and
   a calculating step of calculating the particle size based on the fact that $k_B T/3\pi\eta d$ is proportional to a root mean square value of the displacement where $k_B$ represents a Boltzmann constant, T represents an absolute temperature, $\eta$ represents a viscosity coefficient of the dispersion medium, and d represents the particle size;
   wherein the image analyzing step further includes a step of obtaining a scattered light intensity and a number concentration of a plurality of the particles from the images, and
   the calculating step further includes a step of determining a material of the particles by acquiring a relative refractive index m using a relational expression between a scattered light intensity I which is the intensity of the scattered light and an incident light intensity $I_0$ which is the intensity of the laser light and performing absorption correction, where c represents the number concentration, r represents the distance between the particles and the camera, λ represents a wavelength of the laser light, d represents the particle size, and m represents a relative refractive index of the particles with respect to the dispersion medium:

$$I \propto I_0 \frac{c}{2r^2}\left(\frac{2\pi}{\lambda}\right)^4\left(\frac{d}{2}\right)^6\left|\frac{m^2-1}{m^2+2}\right|^2.$$

5. The particle size measuring method according to claim 4, wherein the dispersion medium is allowed to flow along an axis line in the column, an optical axis of the camera is disposed toward a direction perpendicular to the axis line, and the displacement is acquired by subtracting a moving component due to a flow velocity of the dispersion medium from a moving component in a direction along the axis line of the particles in the images in the image analyzing step.

6. The particle size measuring method according to claim 4, wherein a moving component in a vertical direction and a moving component in a horizontal direction of the corresponding particles in the images are acquired in the image analyzing step, and the particle size of only the corresponding particles in which a difference or a ratio between the root mean square value of the moving component in the vertical direction and the root mean square value of the moving component in the horizontal direction is set to be in a predetermined range is calculated in the calculating step.

* * * * *